United States Patent [19]
Yawata et al.

[11] Patent Number: 5,556,277
[45] Date of Patent: Sep. 17, 1996

[54] FLARED BUCCAL TUBE HAVING AN INTERNALLY TAPERED MESIAL SECTION

[75] Inventors: Haruyasu (Harry) Yawata, Huntington Beach; James J. Hilgers, Laguna Niguel, both of Calif.

[73] Assignee: Ormco Corporation, Glendora, Calif.

[21] Appl. No.: 432,078

[22] Filed: May 1, 1995

[51] Int. Cl.⁶ ............................................. A61C 3/00
[52] U.S. Cl. ............................................................ 433/17
[58] Field of Search ................................. 433/8, 9, 16, 17

[56] References Cited

U.S. PATENT DOCUMENTS

| | | | |
|---|---|---|---|
| Re. 28,962 | 9/1976 | Wallshein | 433/17 |
| 3,874,080 | 4/1975 | Wallshein | 433/16 |
| 4,963,092 | 10/1990 | Snead | 433/17 |
| 5,057,012 | 10/1991 | Kesling | 433/17 |
| 5,151,028 | 9/1992 | Snead | 433/17 |
| 5,292,248 | 3/1994 | Schultz | 433/17 |

*Primary Examiner*—Nicholas D. Lucchesi
*Attorney, Agent, or Firm*—Wood, Herron & Evans

[57] ABSTRACT

This invention is directed to a flared orthodontic buccal tube having an internally tapered mesial section. In a preferred embodiment, the buccal tube includes a base adapted to be secured to a tooth, and a tubular body connected to the base. The tubular body has mesial and distal sections connected at a mesial-distal interface, and mesial and distal bores communicating at a mesial bore-distal bore interface. The mesial section is tapered, with the mesial opening of the mesial bore having cross sectional dimensions exceeding the cross sectional dimensions of the exterior surface of the distal section.

26 Claims, 2 Drawing Sheets

FLARED BUCCAL TUBE HAVING AN INTERNALLY TAPERED MESIAL SECTION

FIELD OF THE INVENTION

This invention is directed to orthodontic buccal tubes, and more particularly, to a buccal tube having a tube or slot with an internally flared mesial section for readily receiving an orthodontic archwire.

BACKGROUND OF THE INVENTION

One of the difficulties for orthodontists in working with buccal tubes is the difficulty of inserting an orthodontic archwire into the archwire passage or bore of the buccal tube. Because orthodontic archwires and archwire-receiving bores are quite small, and buccal tubes are positioned toward the back of the mouth, threading of the orthodontic wires into the bores can be quite challenging. Furthermore, if a tooth is severely maloccluded, such as for example a second bicuspid, it may not be possible to thread an orthodontic wire from a bracket on that tooth through a buccal tube on the adjacent first molar, in which case an orthodontist may have to choose a less desirable treatment option.

U.S. Pat. No. 3,874,080 has sought to address the problem of threading an archwire into a buccal tube by providing a buccal end tube device having two spaced substantially parallel tabs supported on a mounting portion. Each of the parallel tabs is provided with a plurality of apertures for receiving an orthodontic archwire, and the wire-receiving mesial ends of the apertures may be tapered with an internal conical or prismatic taper to facilitate location and entry of an archwire into the respective apertures. The buccal end tube device includes several apertures on each parallel tab so that an orthodontist may choose a set of apertures on the device to exert more or less tooth moving force.

One of the disadvantages of the '080 device is that the tapered wire-receiving ends of the apertures still are relatively small. In addition, once an orthodontist has threaded an archwire through an aperture in the mesial tab, the clinician still must thread the archwire through an aperture in the distal tab. However, because the archwire already has been threaded through the mesial tab, the orthodontist may take only very limited advantage of any taper in the mesial side of the distal tab. Furthermore, because the parallel tabs include a number of different apertures, the overall end tube device is quite large.

Another challenge for orthodontists in the use of buccal tubes is the insertion of auxiliary wires into auxiliary passages or bores. Furthermore, patients wearing extra-oral or intra-oral devices such as headgear or lip bumpers must position the distal ends of a device such as a face bow or lip bumper into an auxiliary passage or bore on the buccal tube appliances, and because of the small size and location of the appliances, proper engagement of an extra-oral or intra-oral device with a buccal tube can be quite difficult.

U.S. Pat. No. 4,963,092 has attempted to address the challenge of inserting an auxiliary wire into a buccal tube by providing a mesial, open-ended cylindrical passage and a distal rectangular passage aligned with the cylindrical passage. The cylindrical passage is larger in diameter than the rectangular passage, and a funnel-shaped wall connects the two passages in order to guide an end of a rectangular wire toward a position within the rectangular passage.

One of the limitations of the '092 appliance is that the funnel-shaped wall connecting the two passages is positioned approximately three-quarters of the way toward the distal end of the appliance. Therefore, an orthodontist is unable to take full advantage of the angle of the funnel-shaped wall when placing a wire into the rectangular passage. Furthermore, the funnel-shaped wall exists only on the inside of the passageway, while the outside diameter of the tube remains large along the entire length of the appliance, resulting in a buccal tube appliance which is not very compact.

U.S. Pat. Nos. 5,057,012 and 5,151,028 have dealt with the face bow-lip bumper issue by providing an internally flared or enlarged mesial opening to enhance insertion of a face bow or lip bumper by a patient. However, the outside diameter of the tube is relatively constant or only very slightly tapered, resulting in a buccal tube appliance with a relatively large overall size.

Therefore, it would be advantageous to have a buccal tube having a passage or bore with an enlarged mesial opening for easier insertion of an orthodontic archwire while maintaining a relatively small overall size to the buccal tube. It also would be desirable to provide an enlarged mesial opening on the auxiliary passage or bore of buccal tubes having an auxiliary passage, where the enlarged opening is achieved while maintaining a small overall size to the auxiliary tube.

SUMMARY OF THE INVENTION

This invention is directed to a buccal tube having a base adapted to be secured to a tube, and a tubular body connected to the base. The tubular body has mesial and distal sections integrally connected at a mesial-distal interface. The mesial and distal sections have mesial and distal ends, respectively, defining the opposite ends of the tubular body. The mesial and distal sections also have mesial and distal bores, respectively, communicating at a mesial bore-distal bore interface. The mesial and distal bores have mesial and distal openings, respectively, at their mesial and distal ends, respectively, and the distal bore has a generally uniform cross-section along its length. Preferably, the mesial bore, distal bore and mesial bore-distal bore interface have a common longitudinal axis.

The mesial section of the tubular body is tapered with the mesial opening of the mesial bore having cross-sectional dimensions exceeding the cross-sectional dimensions of the exterior surface of the distal section. Furthermore, the mesial bore tapers along its length to the mesial bore-distal bore interface.

The distal bore typically has a cross-sectional shape corresponding to the cross-sectional shape of an orthodontic archwire.

In a preferred form, the mesial bore-distal bore interface tapers along its length toward the distal bore, thereby assisting in guiding an orthodontic archwire into the distal bore. Additionally, the mesial bore-distal bore interface preferably has a cross-sectional shape which is substantially circular. This substantially circular and tapered interface enables a distal end of an orthodontic archwire to rotate relatively unhindered about the longitudinal axis of the mesial bore-distal bore interface while seeking a proper rotational alignment with the cross-sectional shape of the distal bore.

In a preferred embodiment of the buccal tube, the mesial bore tapers along its length at an angle which varies relative to the common longitudinal axis of the mesial bore, distal bore and mesial bore-distal bore interface, as described more fully in the detailed description below. Although other angles may be used, these angles are particularly advantageous in providing a buccal tube which is compact, yet which provides an enlarged mesial opening and tapered bore.

In a preferred form of the invention, the cross-sectional dimensions of the mesial opening are about 2.3 to 3.1 times larger than the cross-sectional dimensions of the distal bore, and about 2.4 to 3.6 times larger than the length of the mesial bore along its longitudinal axis. Also, the cross-sectional dimensions of the mesial opening preferably are about 1.1 to 1.4 times larger than the cross-sectional dimensions of the exterior surface of the distal section, and about 1.8 to 3.1 times larger than the cross-sectional dimensions of the mesial bore-distal bore interface.

In terms of specific dimensions, in a preferred embodiment, the mesial opening has cross-sectional dimensions of from about 0.06 in. to about 0.10 in., the distal bore has cross-sectional dimensions of from about 0.02 in. to about 0.03 in., and the mesial bore has a length along its longitudinal axis of from about 0.02 in. to about 0.03 in. Also, in a preferred embodiment, the external surface of the distal section has cross-sectional dimensions of from about 0.05 in. to about 0.06 in., the mesial bore-distal bore interface has cross-sectional dimensions of from about 0.02 in. to about 0.04 in., and the distal section has a length of from about 0.12 in. to about 0.16 in. In a particularly preferred embodiment, the mesial opening has cross sectional dimensions of from about 0.069 in. to about 0.075 in., the mesial bore has a length along its longitudinal axis of about 0.025 in., and the distal section has a length of about 0.13 in.

If desired, the buccal tube also may include an auxiliary tubular body for receiving an auxiliary wire, face bow or lip bumper, with the auxiliary tubular body being in substantially side-by-side relationship with the tubular body. Furthermore, this auxiliary tubular body also may have a tapered mesial section according to the principles of the invention, with the auxiliary mesial opening of the auxiliary mesial bore having cross-sectional dimensions exceeding the cross-sectional dimensions of the exterior surface of the auxiliary distal section.

In another embodiment of the invention, the buccal tube includes a base adapted to be secured to a tooth, a body connected to the base and having an archwire slot or bore for receiving an orthodontic archwire, and an auxiliary tubular body being in substantially side-by-side relationship with the body. In this particular embodiment, the primary archwire-receiving slot or bore may be a conventional tapered slot or bore. The passage may be permanently closed on all sides, having a mesial opening and a distal opening. Or, if desired, the passage may be an archwire slot, with or without a removable cap for covering the archwire slot. The tubular auxiliary body, on the other hand, includes a tapered mesial section according to the principles of the invention, with the mesial opening of the mesial bore having cross-sectional dimensions exceeding the cross-sectional dimensions of the exterior surface of the distal section.

The buccal tubes of the present invention offer several benefits and advantages. For example, because the inventive buccal tube provides a tapered mesial section and bore in an appliance which is relatively compact overall, an orthodontist is able to use the buccal tube in a wider range of cases. The flared mesial bore allows an orthodontist to approach the distal bore with an archwire from any of a number of different angles. Furthermore, regardless of the level of malocclusion, the enlarged mesial opening and flared mesial bore provide an enlarged target area for an orthodontist who is attempting to thread a tiny orthodontic archwire into an opening in a buccal tube which is positioned toward the back of the mouth.

In addition, the inventive buccal tube provides an enlarged target area for a patient who is trying to insert an extra-oral or intra-oral device such as a face bow, lip bumper or the like into an auxiliary opening of the buccal tube. And regardless of whether the flared mesial section and bore are provided on the tubular body, auxiliary tubular body or both, the flared design is achieved in a buccal tube which still is extremely compact, thereby maintaining patent comfort.

DETAILED DESCRIPTION OF THE INVENTION

Figure 1:
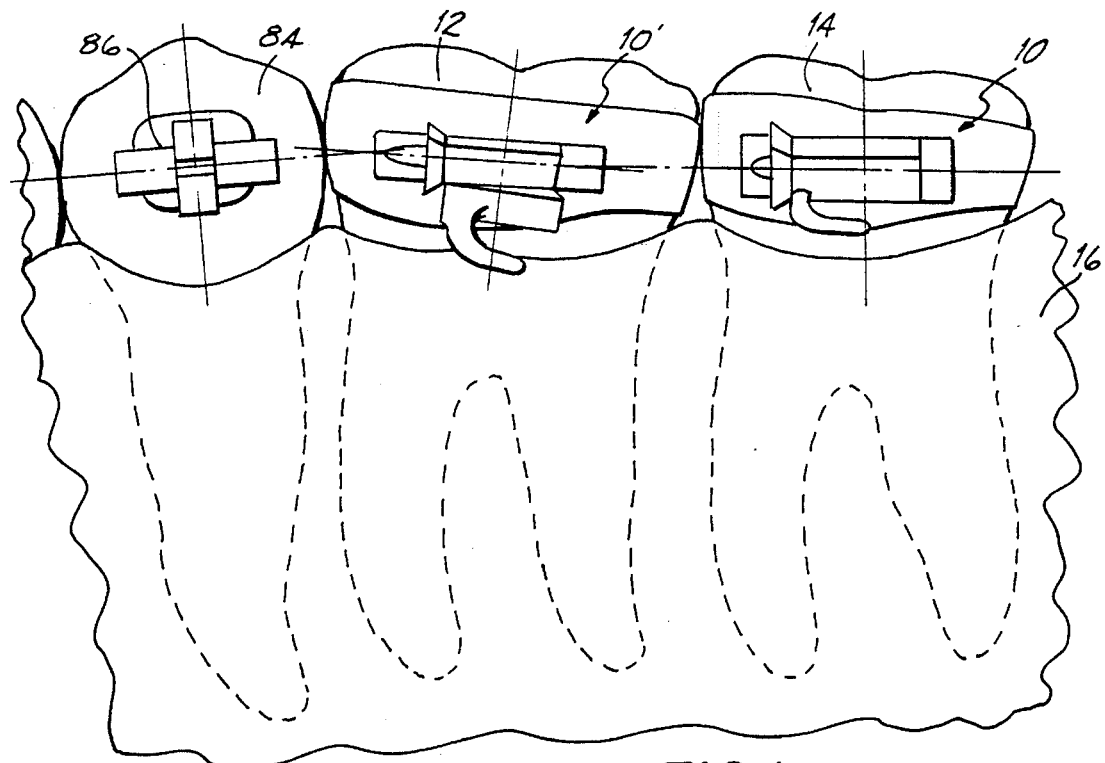
FIG. 1 is a buccal view of two buccal tubes according to the present invention, placed on a first molar and second molar of the mandibular jaw.

Referring to FIG. 1, buccal tubes 10, 10' according to the principles of the invention are shown installed on a first molar 12 and a second molar 14 of the mandibular arch 16. More specifically, referring to FIGS. 2–4, one embodiment of the inventive buccal tube 10 includes a base 18 adapted to be secured to a tooth, and a tubular body 20 connected to the base 18. The tubular body 20 has mesial and distal sections 22, 24 integrally connected at a mesial-distal interface 26, with the mesial section 22 having a mesial end 28 and the distal section 24 having a distal end 30 defining the opposite ends of the tubular body 20. Furthermore, the mesial and distal sections 22, 24 have mesial and distal bores 32, 34, respectively, which communicate at a mesial bore-distal bore interface 36. The mesial bore 32 has a mesial opening 38 at the mesial end 28, and the distal bore 34 has a distal opening 40 at the distal end 30. The distal bore has a generally uniform cross section along its length and has a cross sectional shape corresponding to the cross sectional shape of a rectangular orthodontic archwire 42. In order to facilitate threading of an orthodontic archwire into the buccal tube 10 while maintaining the buccal tube's compact size, the mesial section 22 of the tubular body 20 is flared, with the mesial opening 38 having cross sectional dimensions exceeding the cross sectional dimensions of the exterior surface 44 of the distal section 24, and the mesial bore 32 tapering along its length to the mesial bore-distal bore interface 36.

Figure 2:
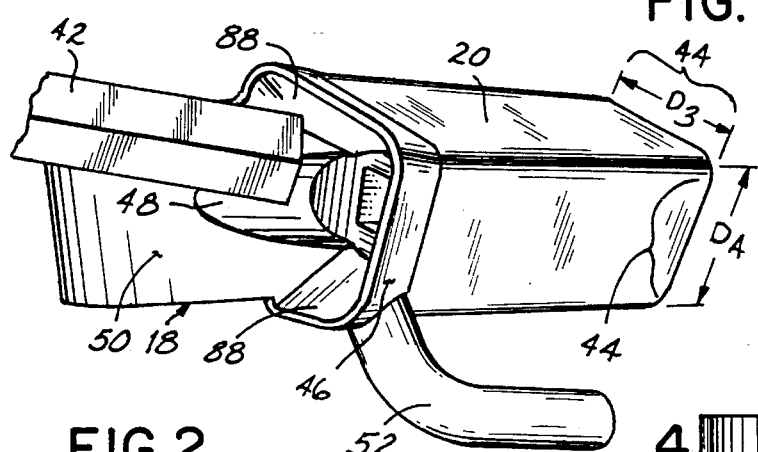
FIG. 2 is a perspective view of an embodiment of the flared buccal tube.
Figure 3:
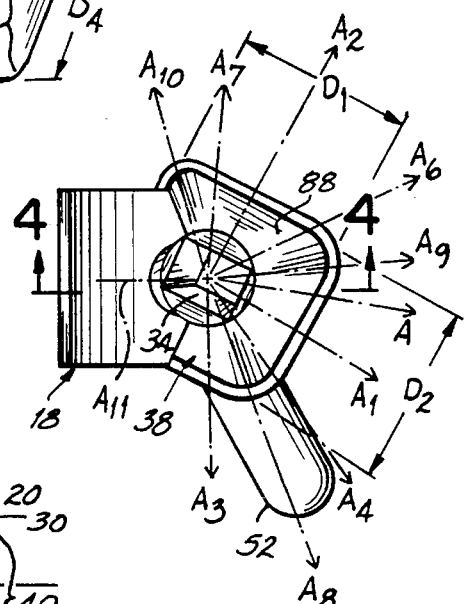
FIG. 3 is a mesial end view of the flared buccal tube of FIG. 2.
Figure 4:
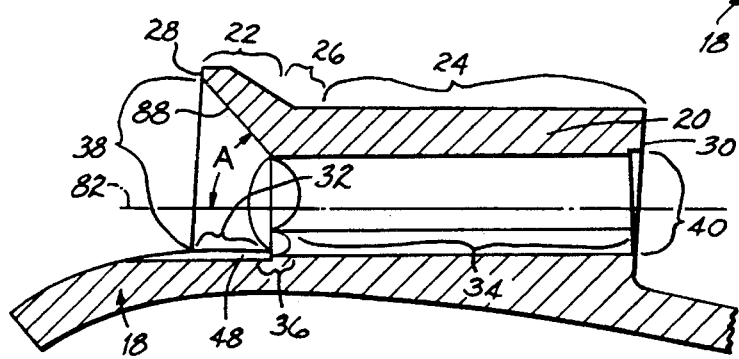
FIG. 4 is a cross-sectional view of the flared buccal tube of FIG. 3 taken along line 4—4.

As shown in FIGS. 2–4, in a preferred embodiment of the invention, the mesial bore-distal bore interface 36 has a cross sectional shape which is substantially circular and which tapers along its length toward the distal bore 34, This feature of the invention is particularly advantageous for a buccal tube having a distal bore with a non-circular cross sectional shape. For example, the buccal tube 10 shown in FIGS. 2–4 includes a distal bore 34 having a cross sectional shape which is rectangular, thereby enabling an orthodontist to use a rectangular archwire 42 in generating a torquing force. The substantially circular cross sectional shape of the mesial bore-distal bore interface 36 allows an orthodontist to rotate the distal end of an orthodontic archwire in a relatively unhindered fashion about the longitudinal axis of the mesial bore-distal bore interface 36 while seeking a proper rotational alignment of the archwire with the cross sectional shape of the distal bore 34, In addition, because the mesial bore-distal bore interface 36 tapers along its length toward the distal bore 34, an orthodontist is able to guide an orthodontic archwire into the distal end relatively easily.

The preferred embodiment of FIGS. 2–4 includes other features as well. For example, the cross sectional shape of the exterior surface 46, 44 of the mesial and distal sections 22, 24 of the tubular body 20 is substantially rectangular. This rectangular shape enables the buccal tube 10 to be smaller in overall size than a buccal tube having a generally cylindrical or rounded exterior cross sectional shape, thereby providing a flared buccal tube having a low profile in the mouth, The buccal tube 10 also includes a scoop-out trough 48 formed in the upper surface 50 of the base 18. This scoop-out 48 allows the mesial and distal bores 32, 34 to be positioned closer to the base 18, thereby further reducing the size and profile of the buccal tube 10. In addition, the buccal tube 10 includes a hook 52 for attaching an elastic band, ligature wire or the like.

Buccal tubes according to the present invention offer the advantage of an enlarged mesial target area for guiding an orthodontic archwire into a buccal tube, while maintaining relatively small dimensions throughout the tubular body.

The mesial bore may be tapered along its length at any of a number of different angles relative to the common longitudinal axis of the mesial bore, distal bore and mesial bore-distal bore interface. Referring to FIG. 4, in a preferred embodiment of the buccal tube, the mesial bore tapers along its length at an angle, A, relative to the common longitudinal axis 82, which angle A varies depending upon the particular portion of the interior surface 88 of the mesial section 22 being considered in forming the angle A. Referring to FIGS. 3 and 4, the angle A formed between the common longitudinal axis 82 and the interior surface 88 of the mesial section 22: along ray $A_1$ or $A_2$ is about 35°; along ray $A_3$, $A_4$, $A_5$, $A_6$ or $A_7$ is about 45°; along ray $A_8$, $A_9$, or $A_{10}$ is slightly greater than 45°; and along ray $A_{11}$ is about 5°. The angle A changes gradually between locations $A_1$ and $A_{11}$.

This range of angles provides a good balance between having an enlarged mesial opening or target for readily guiding an orthodontic archwire into a buccal tube, and maintaining relatively small overall dimensions to the buccal tube. In terms of specific dimensions, in a preferred embodiment, the mesial opening has cross-sectional dimensions of from about 0.06 in. to about 0.10 in. when measured along line $D_1$ or $D_2$ as shown in FIG. 3, the distal bore has cross-sectional dimensions of from about 0.02 in. to about 0.03 in., and the mesial bore has a length along its longitudinal axis of from about 0.02 in. to about 0.03 in. Also, in a preferred embodiment, the external surface of the distal section has cross-sectional dimensions of from about 0.05 in. to about 0.06 in. when measured along line $D_3$ or $D_4$ of FIG. 2, the mesial bore-distal bore interface has cross-sectional dimensions of from about 0.02 in. to about 0.04 in., and the distal section has a length of from about 0.12 in. to about 0.16 in. In a particularly preferred embodiment, the mesial opening has cross sectional dimensions of from about 0.069 in. to about 0.075 in., the mesial bore has a length along its longitudinal axis of about 0.025 in., and the distal section has a length of about 0.13 in.

Figure 5:
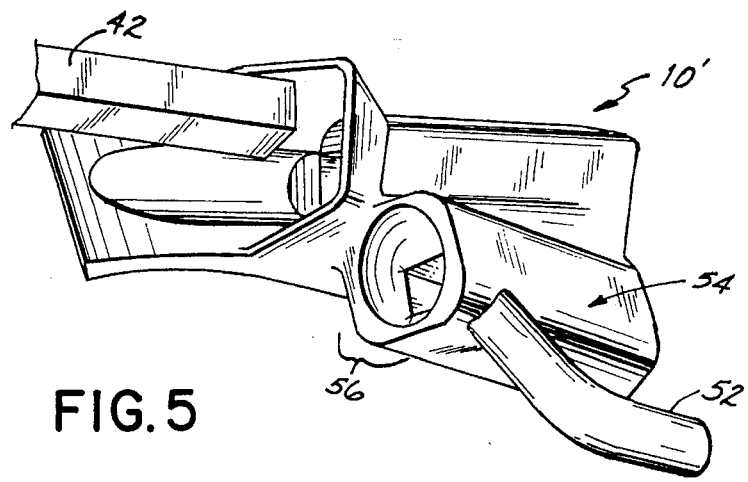
FIG. 5 is a perspective view of another embodiment of the flared buccal tube.
Figure 6:
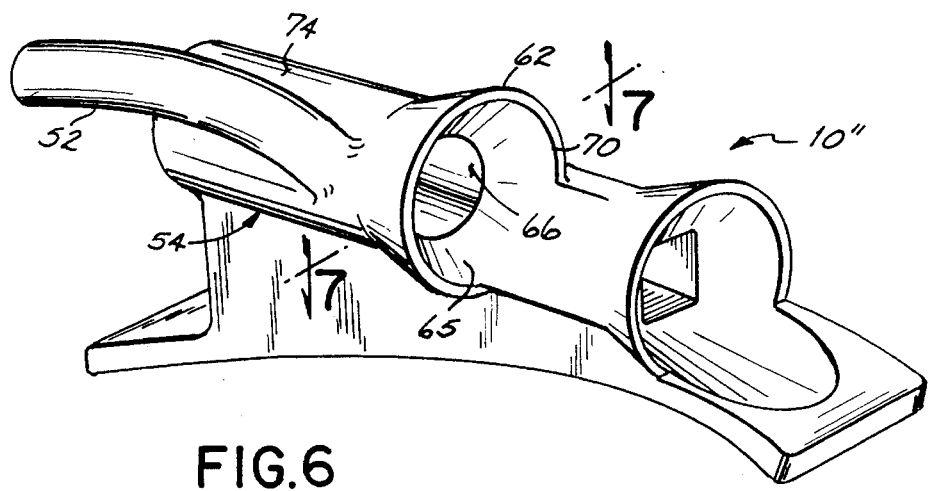
FIG. 6 is a perspective view of yet another embodiment of the flared buccal tube.
Figure 7:
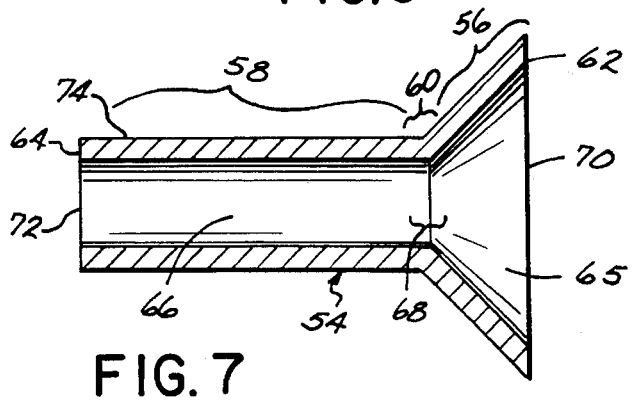
FIG. 7 is a cross-sectional view of the flared buccal tube of FIG. 6 taken along line 7—7.

If desired, the flared buccal tube also may include an auxiliary tubular body for receiving an auxiliary wire, face bow or lip bumper. For the convenience of the reader, elements in the following embodiments similar to elements in FIGS. 2–4 are given like numbers. As shown in FIG. 5, the auxiliary tubular body 54 may be a conventional tubular body having an untapered mesial section 56. However, if desired, the auxiliary tubular body may have a tapered mesial section enabling an orthodontist or patient to guide an auxiliary wire, face bow or lip bumper into the auxiliary tubular body more easily. For example, FIGS. 6–7 illustrate a buccal tube 10" having a tubular body 20 and an auxiliary tubular body 54, both of which are tapered according to the principles of the invention. More specifically, the auxiliary tubular body 54 includes mesial and distal sections 56, 58 integrally connected at a mesial-distal interface 60. The mesial section 56 has a mesial end 62 and the distal section 58 has a distal end 64 defining the opposite ends of the auxiliary tubular body 54. Furthermore, the mesial and distal sections 56, 58 have mesial and distal bores 65, 66, respectively, communicating at a mesial bore-distal bore interface 68. The mesial bore 65 has a mesial opening 70 at its mesial end 62 and the distal bore 66 has a distal opening 72 at its distal end 64. In addition, the distal bore 66 has a generally uniform cross section along its length.

The mesial section 56 of the auxiliary tubular body 54 is tapered, with the mesial opening 70 of the mesial bore 65 having cross sectional dimensions exceeding the cross sectional dimensions of the exterior surface 74 of the distal section 58. Furthermore, the mesial bore 65 tapers along its length to a cross section at the mesial bore-distal bore interface 68.

Figure 8:
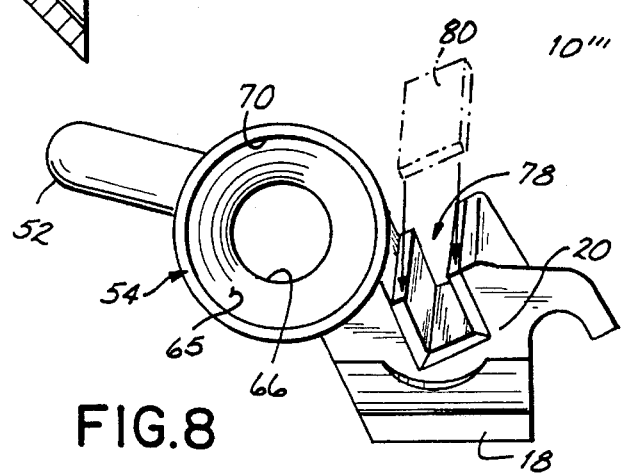
FIG. 8 is a mesial end view of a further embodiment of the flared buccal tube.

In yet another embodiment of the inventive buccal tube, the buccal tube includes a traditional unflared tubular body or archwire slot for receiving an orthodontic archwire. However, the auxiliary tubular body is flared according to the principles of the invention, thereby making insertion of an auxiliary wire, face bow or lip bumper relatively easy. For example, referring to FIG. 8, a convertible buccal tube 10''' is shown having a base 18, a body 20 connected to the base 18 and an auxiliary tubular body 54 in side-by-side relationship with the body 20. The base 18 is adapted to be secured to a tooth, and the body 20 has an archwire slot 78 for receiving an orthodontic archwire. As shown, the body 20 further includes a removable cap 80 (shown in a detached position) for converting the primary tubular body 20 into an archwire slot 78. The auxiliary tubular body 54 has a longitudinal cross section similar to that shown in FIG. 7.

The flared buccal tubes of the present invention may be made by investment molding. In this process, preliminary plastic buccal tubes are formed by injecting molten polystyrene into an injection mold made of metal. Once these plastic buccal tubes have been formed, they are removed from the mold and prepared for encapsulation in an investment mold by orienting the plastic buccal tubes on a wax frame. At this point, the wax frame and plastic buccal tubes are encapsulated into an investment mold which is made out of platinite. Then, once the investment mold has been formed, molten metal is poured into the investment mold to form the actual metal buccal tubes for use in the mouth. The molten metal burns away the plastic and wax in forming the metal buccal tubes. Once the metal has hardened, the platinite investment mold simply is broken away, revealing the finished buccal tubes. At this point, the buccal tubes may be removed from the metal sprue and polished or buffed as needed.

The inventive buccal tubes may be used as any traditional buccal tube would be used. However, because of the inventive design of these buccal tubes, they are much more user-friendly. For example, because the buccal tube has an enlarged mesial opening, an orthodontist may guide the distal end of an orthodontic archwire into the tubular body relatively easily. Furthermore, a patient is able to guide the distal ends of a face bow or lip bumper into the flared mesial section of an auxiliary tubular body on the buccal tube relatively easily as well. Moreover because the flared mesial section is designed so as to preserve the small overall size of the buccal tube, this easy archwire threading is provided without compromising patient comfort of the buccal tube appliance in the mouth.

The flared design also allows the inventive buccal tube to be used in treatment situations previously inappropriate for buccal tube appliances. For example, many orthodontists would like to employ buccal tubes on both the first and second molars in providing orthodontic treatment to patients. The buccal tubes are preferred because they may be smaller than many of the orthodontic brackets which are used. However, if a second bicuspid or first or second molar is significantly maloccluded, it is extremely difficult, if not impossible, to thread an orthodontic archwire through a traditional buccal tube on the first or second molar. Therefore, an orthodontist is forced to compromise, for example, by using the archwire slot of a significantly larger convertible buccal tube on the first molar. However, when buccal tubes of the present invention are used, there is no need to compromise in these treatment situations. For example, referring to FIG. 1, a second bicuspid 84, first molar 12 and second molar 14 of the mandibular jaw 16 are shown. The second bicuspid 84 and first molar 12 are maloccluded, making the threading of an archwire into a traditional buccal tube extremely difficult. However, the buccal tubes 10,10' shown in FIG. 1 employ the inventive flared mesial section, thereby making it possible for an orthodontist to thread an orthodontic archwire from a bracket 86 on the second bicuspid 84 through both buccal tubes 10,10'.

Although the invention has been discussed in detail above with respect to a few particular embodiments, it is to be understood that the scope of the invention is to be determined by the following claims.

What is claimed is:

1. A buccal tube, comprising:
   a base adapted to be secured to a tooth; and
   a tubular body connected to said base, said tubular body having mesial and distal sections integrally connected at a mesial-distal interface, said mesial and distal sections having mesial and distal ends, respectively, defining the opposite ends of said tubular body, said mesial and distal sections having mesial and distal bores, respectively, communicating at a mesial bore-distal bore interface, said mesial and distal bores having mesial and distal openings, respectively, at their mesial and distal ends, respectively, said distal section having an exterior surface,
   said mesial section being tapered, with said mesial opening of said mesial bore having cross-sectional dimensions exceeding the cross-sectional dimensions of the exterior surface of said distal section, said mesial bore tapering along its length to said mesial bore-distal bore interface.

2. The buccal tube of claim 1 wherein said mesial bore, distal bore and mesial bore-distal bore interface have a common longitudinal axis.

3. The buccal tube of claim 1 wherein said distal bore has a cross-sectional shape corresponding to the cross-sectional shape of an orthodontic archwire.

4. The buccal tube of claim 1 wherein said mesial bore-distal bore interface tapers along its length toward said distal bore, thereby assisting in guiding an orthodontic archwire into said distal bore.

5. The buccal tube of claim 4 wherein said mesial bore-distal bore interface has a cross-sectional shape which is substantially circular, thereby enabling a distal end of an orthodontic archwire to rotate relatively unhindered about the longitudinal axis of said mesial bore-distal bore interface while seeking a proper rotational alignment with the cross-sectional shape of said distal bore.

6. The buccal tube of claim 1 wherein said mesial bore-distal bore interface has a cross-sectional shape which is substantially circular and which tapers along its length toward said distal bore, thereby enabling a distal end of an orthodontic archwire to rotate relatively unhindered about the longitudinal axis of said mesial bore-distal bore interface while seeking a proper rotational alignment with the cross-sectional shape of said distal bore.

7. The buccal tube of claim 1 wherein said mesial bore tapers along its length at an angle of about 45° relative to the common longitudinal axis of said mesial bore, distal bore and mesial bore-distal bore interface.

8. The buccal tube of claim 1 wherein the cross-sectional dimensions of said mesial opening are about 2.3 to 3.1 times larger than the cross-sectional dimensions of said distal bore and about 2.4 to 3.6 times larger than the length of said mesial bore along its longitudinal axis.

9. The buccal tube of claim 8 wherein the cross-sectional dimensions of said mesial opening are about 1.1 to 1.4 times larger than the cross-sectional dimensions of the exterior surface of said distal section.

10. The buccal tube of claim 8 wherein the cross-sectional dimensions of said mesial opening are about 1.8 to 3.1 times larger than the cross-sectional dimensions of said mesial bore-distal bore interface.

11. The buccal tube of claim 1 wherein said mesial opening has cross-sectional dimensions of from about 0.06 in. to about 0.10 in., said distal bore has cross-sectional dimensions of from about 0.02 in. to about 0.03 in., and said mesial bore has a length along its longitudinal axis of from about 0.02 in. to about 0.03 in.

12. The buccal tube of claim 11 wherein the external surface of said distal section has cross-sectional dimensions of from about 0.05 in. to about 0.06 in.

13. The buccal tube of claim 11 wherein said mesial bore-distal bore interface has cross-sectional dimensions of from about 0.02 in. to about 0.04 in.

14. The buccal tube of claim 1 further including an auxiliary tubular body for receiving an auxiliary wire, face bow or lip bumper, said auxiliary tubular body being in substantially side-by-side relationship with said tubular body.

15. The buccal tube of claim 14 wherein said auxiliary tubular body includes:
   mesial and distal sections integrally connected at a mesial-distal interface, said mesial and distal sections of said auxiliary tubular body having mesial and distal ends respectively defining the opposite ends of said auxiliary tubular body said mesial and distal sections of said auxiliary tubular body having mesial and distal bores respectively, communicating at a mesial bore-distal bore interface, said mesial and distal bores of said auxiliary tubular body having mesial and distal openings, respectively at their mesial and distal ends, respectively, said distal section of said auxiliary tubular body having an exterior surface, said mesial section of said auxiliary tubular body being tapered, with said mesial opening of said mesial bore of said auxiliary tubular body having cross-sectional dimensions exceeding the cross-sectional dimensions of the exterior surface of said distal section of said auxiliary tubular body, said mesial bore of said auxiliary tubular body tapering along its length to said mesial bore-distal bore interface of said auxiliary tubular body.

16. The buccal tube of claim 15 wherein said distal bore of said auxiliary tubular body has a generally uniform cross-section along its length.

17. The buccal tube of claim 1 wherein said distal bore has a generally uniform cross-section along its length.

18. A buccal tube, comprising:

a base adapted to be secured to a tooth;

a body connected to said base and having an element for receiving an orthodontic archwire, said element selected from the group consisting of an archwire slot having a bottom wall and two opposing sidewalls extending therefrom, and a tubular body having a bore; and an auxiliary tubular body being in substantially side-by-side relationship with said body, said auxiliary tubular body having mesial and distal sections integrally connected at a mesial-distal interface, said mesial and distal sections having mesial and distal ends, respectively, defining the opposite ends of said auxiliary tubular body, said mesial and distal sections having mesial and distal bores, respectively, communicating at a mesial bore-distal bore interface, said mesial and distal bores having mesial and distal openings, respectively, at their mesial and distal ends, respectively, said distal section having an exterior surface, said mesial section being tapered, with said mesial opening of said mesial bore having cross-sectional dimensions exceeding the cross-sectional dimensions of the exterior surface of said distal section, said mesial bore tapering along its length to said mesial bore-distal bore interface.

19. The buccal tube of claim 18 wherein said mesial bore, distal bore and mesial bore-distal bore interface have a common longitudinal axis.

20. The buccal tube of claim 18 wherein said distal bore has a cross-sectional shape corresponding to the cross-sectional shape of an auxiliary wire, face bow or lip bumper.

21. The buccal tube of claim 18 wherein said mesial bore-distal bore interface tapers along its length toward said distal bore, thereby assisting in guiding an auxiliary wire, face bow or lip bumper into said distal bore.

22. The buccal tube of claim 21 wherein said mesial bore-distal bore interface has a cross-sectional shape which is substantially circular, thereby enabling a distal end of an auxiliary wire, face bow or lip bumper to rotate relatively unhindered about the longitudinal axis of said mesial bore-distal bore interface while seeking a proper rotational alignment with the cross-sectional shape of said distal bore.

23. The buccal tube of claim 18 wherein said mesial bore-distal bore interface has a cross-sectional shape which is substantially circular and which tapers along its length toward said distal bore, thereby enabling a distal end of an auxiliary wire, face bow or lip bumper to rotate relatively unhindered about the longitudinal axis of said mesial bore-distal bore interface while seeking a proper rotational alignment with the cross-sectional shape of said distal bore.

24. The buccal tube of claim herein said mesial bore tapers along its length at an angle of about 45° relative to the common longitudinal axis of said mesial bore, distal bore and mesial bore-distal bore interface.

25. The buuccal tube of claim 18 wherein said body includes a removable cap.

26. The buccal tube of claim 18 wherein said distal bore has a generally uniform cross-section along its length.

* * * * *